United States Patent
Aly

(10) Patent No.: US 10,993,970 B2
(45) Date of Patent: May 4, 2021

(54) MEDICAL-GRADE HONEY FOR GROWTH ENHANCEMENT OF INFANTS

(71) Applicant: Hany Z. Aly, Alexandria, VA (US)

(72) Inventor: Hany Z. Aly, Alexandria, VA (US)

( * ) Notice: Subject to any disclaimer, the term of this patent is extended or adjusted under 35 U.S.C. 154(b) by 0 days.

(21) Appl. No.: 16/469,214

(22) PCT Filed: Dec. 13, 2017

(86) PCT No.: PCT/US2017/066005
§ 371 (c)(1),
(2) Date: Jun. 13, 2019

(87) PCT Pub. No.: WO2018/118558
PCT Pub. Date: Jun. 28, 2018

(65) Prior Publication Data
US 2019/0381109 A1    Dec. 19, 2019

Related U.S. Application Data

(60) Provisional application No. 62/436,246, filed on Dec. 19, 2016.

(51) Int. Cl.
| | | |
|---|---|---|
| *A61K 36/00* | (2006.01) | |
| *A61K 35/644* | (2015.01) | |
| *A23L 21/25* | (2016.01) | |
| *A23L 33/125* | (2016.01) | |
| *A23L 33/00* | (2016.01) | |
| *A23C 9/20* | (2006.01) | |
| *A61K 9/00* | (2006.01) | |

(52) U.S. Cl.
CPC ............ *A61K 35/644* (2013.01); *A23C 9/206* (2013.01); *A23L 21/25* (2016.08); *A23L 33/125* (2016.08); *A23L 33/40* (2016.08); *A61K 9/0029* (2013.01); *A61K 9/0095* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2009/0053380 A1* | 2/2009 | Petersen | ........... A23L 21/20 426/573 |
| 2012/0171166 A1 | 7/2012 | Chow et al. | |
| 2014/0199431 A1 | 7/2014 | Sliwinski et al. | |
| 2015/0086622 A1 | 3/2015 | Shehadeh et al. | |

FOREIGN PATENT DOCUMENTS

CN            101700066 A   *  5/2010

OTHER PUBLICATIONS

Boyar, Clinical experience with Leptospermum honey use for treatment of hard to heal neonatal wounds: case series. Journal of perinatology: official journal of the California Perinatal Association, (Feb. 2014) vol. 34, No. 2, pp. 161-163 (Year: 2014).*

Drouet, Honey-sweetened milk in nutrition of premature infants and mentally retarded children. OUEST MED., (1963) vol. 16, No. 9, pp. 485-490 (Year: 1963).*

Szentkiralyi et al, Effect of honey on the weight increase in premature infants. Gyermekorvos Szakcsoportjanak folyoirata= Pediatriia,(Jul. 1954) vol. 5, No. 7, pp. 203-209 (Year: 1954).*

* cited by examiner

*Primary Examiner* — Qiuwen Mi
(74) *Attorney, Agent, or Firm* — W&C IP

(57) ABSTRACT

Prebiotic compositions for infants containing medical-grade honey are provided. Methods of supplementing infant milk formula or breast milk with medical-grade honey to enhance growth and improve colonic microbiota are also provided.

9 Claims, 2 Drawing Sheets

MEDICAL-GRADE HONEY FOR GROWTH ENHANCEMENT OF INFANTS

BACKGROUND OF THE INVENTION

Field of the Invention

The invention generally relates to the administration of bee honey to infants, for example, through supplementation of infant milk formula or breast milk. In particular, the invention provides medically-graded honey that is useful for improving colonic microbiota and inducing weight gain and brain growth in newborns and infants.

Background of the Invention

Bifidobacteria is the dominant florum in the intestine of breast-fed infants. Breast milk contains various compounds that are considered prebiotic substances. Prebiotics are non-digestible food compounds that can selectively stimulate the growth of a number of beneficial bacteria in the colon of the host. These prebiotic ingredients can relatively protect against infections in breast fed infants. It contains approximately 1% oligosaccharides whereas cow's milk contains negligible amounts of oligosaccharides. Glucose, galactose, N-acetylglucosamine, fructose and sialic acid constitute the building units for >130 prebiotic compounds in breast milk. These compounds inhibit both gram positive and gram negative pathogenic bacteria and contribute towards its anti-infective properties.

Preterm infants develop a portfolio of intestinal microbiota that differs largely from full term infants regardless of being fed breast milk or milk formula. Enterobacteriaciae, enterococci, clostridia, staphylococci and yeasts are the predominant intestinal organisms in preterm infants whereas bifidobacteria are significantly less common. These differences could be attributed to decreased exposure to the maternal microbiota, increased exposure to hospital organisms, use of antibiotics, and delayed enteral feeding.

The absence of protective microbiota in the intestine of premature infants is yet another challenge to their growth; the gastrointestinal barrier function, gut motility, mucosal immunity, and the digestive and absorptive capacity are all underdeveloped in this population, thereby increasing their risk of nosocomial infections and necrotizing enterocolitis (NEC). Therefore, modifying the intestinal microbiota to more closely resemble that of term breast-fed infants has been a focus of research. Interest in bifidogenic diets has increased after the findings that demonstrated the addition of bifidobacteria to infant formula could reduce the risk and severity of necrotizing enterocolitis and the incidence of allergic diseases in preterm infants.

Honey is a natural product with a very complex chemical composition that includes primarily fructose, glucose and to a less extent (4-5%) fructo-oligosaccharides that can serve as prebiotics. It contains more than 180 substances, including amino acids, vitamins, minerals and enzymes. The consumption of honey is not encouraged for infants less than 12 months of age because of the risk to develop infantile botulism in the event that it is contaminated with the spores of *Clostridium botulinum*.

SUMMARY OF THE INVENTION

The present disclosure provides methods of administering honey to infants and infant milk formulas or breast milk supplemented with honey. The risk of botulism is avoided by using medical-grade, spore-free honey. Administration of medical-grade honey to infants induces weight gain, brain growth and changes in colonic microbiota in infants.

One aspect of the invention provides a method for enhancing growth in an infant comprising administering to said infant medical-grade honey in an amount sufficient to enhance growth in said infant. In some embodiments, the infant is a low birth weight infant and/or was born prematurely. In some embodiments, the medical-grade honey is administered with infant milk formula or breast milk. In further embodiments, the amount of medical-grade honey is an amount sufficient to increase the weight and/or increase the head circumference of said infant. In some embodiments, the amount is at least 5 grams of medical-grade honey per day. In further embodiments, the method further comprises simultaneously or sequentially administering parenteral nutrition to said infant.

Another aspect of the invention provides a method for promoting growth of non-pathogenic intestinal microbiota in an infant comprising administering to said infant medical-grade honey in an amount sufficient to promote growth of non-pathogenic intestinal microbiota in said infant. In some embodiments, the non-pathogenic intestinal microbiota includes at least one of *Bifidobacterium* and Lactobacilli. In some embodiments, the amount is an amount sufficient to decrease the growth of intestinal pathogens such as Enterobacteriaceae and Staphylococci. In further embodiments, the infant is a low birth weight infant and/or was born prematurely. In additional embodiments, the medical-grade honey is administered with infant milk formula or breast milk. In some embodiments, the amount is at least 5 grams of medical-grade honey per day. In some embodiments, the method further comprises the step of simultaneously or sequentially administering parenteral nutrition to said infant.

Another aspect of the invention provides a prebiotic composition comprising infant milk formula and medical-grade honey. In some embodiments, the medical-grade honey is present in a concentration of at least 10 mg/ml.

DETAILED DESCRIPTION

Figure 1:
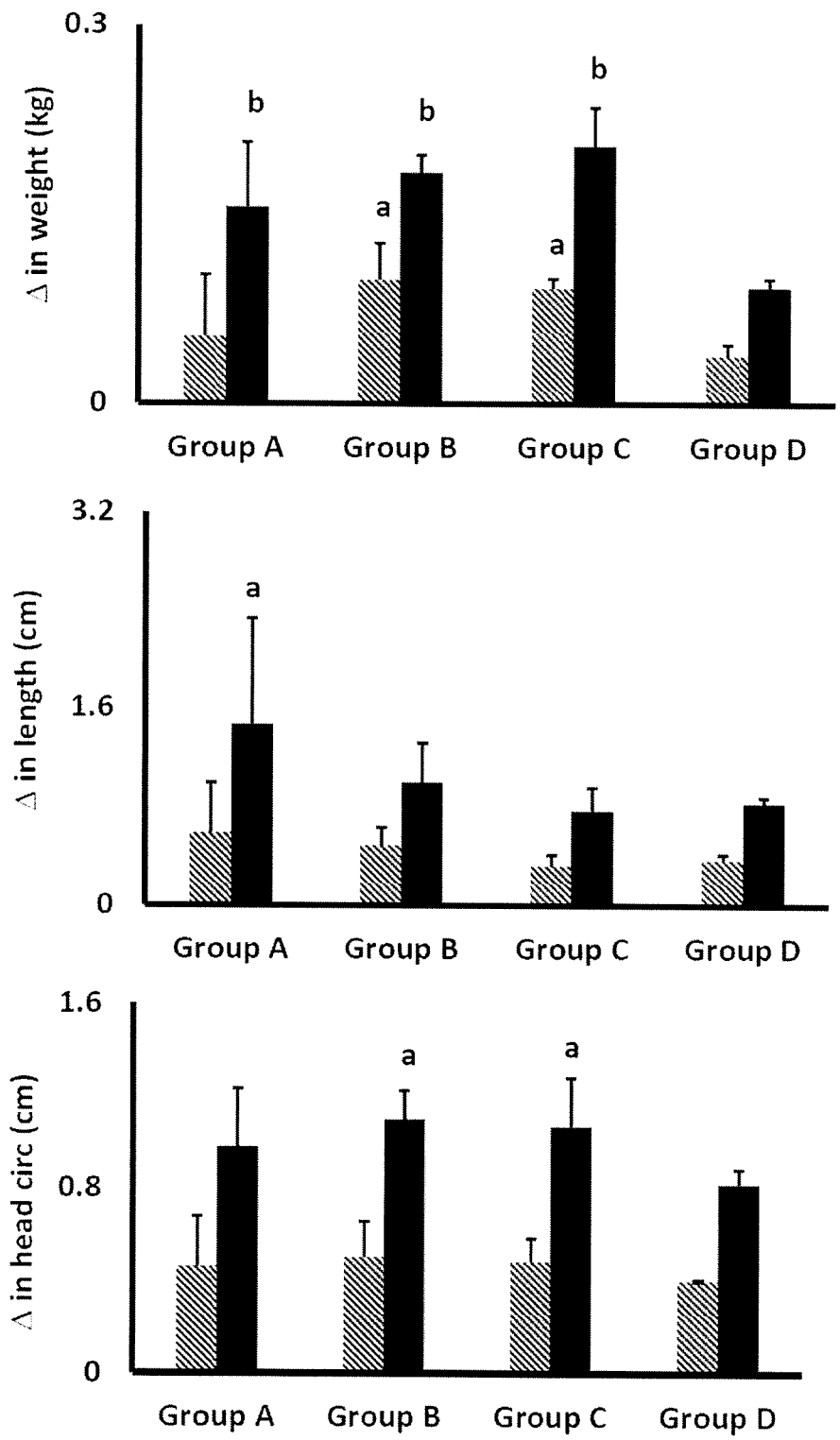
FIG. 1. Changes in anthropometric measurements in the 4 study groups after one and two weeks of enrollment. Dashed bars represent changes between baseline and one week. Solid bars represent changes between baseline and two weeks. Upper panel represents changes in weight, (a): compared to the control group, groups B and C had significant increase in weight after one week ($p<0.0001$), and (b): compared to the control group, groups A, B and C had significant weight increase after two weeks ($p<0.0001$). Middle panel represents changes in length, (a): group A had greater increase in length compared to control group after two weeks ($p=0.009$). Lower panel represents changes in head circumference, (a): head circumference increased significantly in groups B and C when compared to group D after two weeks ($p=0.0056$).

Aspects of the invention relate to medically-graded enteral honey administration and its effect on intestinal microbiota, immune response, and somatic growth of infants. Administration of honey alone or as a supplement of milk formula or breast milk results in changes in the physical growth and colonic microbiota of infants. In particular, consumption of honey leads to enhanced growth evidenced by increased weight gain and head circumference. Further, infants who receive honey have increased colonization of "good" (having a positive effect on the health of a patient) non-pathogenic intestinal microbiota such as *Bifidobacterium* and Lactobacilli and decreased colonization of "bad" (having a negative effect on the health of a patient) intestinal microbiota such as *Enterobacteriaceae*.

"Infant" means a subject ranging in age from birth to about one to two years and includes infants from 0 to about 12-24 months corrected age. In some embodiments, the infant is a low birth weight infant (i.e. weighing less than 2500 grams), a very low birth weight infant (i.e. weighing less than 1500 grams), an extremely low birth weight infant (i.e. weighing less than 1000 grams) and/or a preterm infant. "Preterm" or "premature" infant means a subject born at a gestational age of less than or equal to 37 weeks. Gestational age may be estimated using the last menstrual date, ultrasonography, or the Ballard scoring system performed in the first day of life.

The term "enhancing growth in an infant" refers to an increase of at least one of body weight, height, and head circumference. Enhancing the growth or growth rate also comprises a measure above the expected for the preterm or low birth weight infant for gastrointestinal maturation. According to certain embodiments, the measure of the infant gastrointestinal maturation is set by the number of days required to achieve complete enteral feed, i.e. an enteral feed at an amount of about 130-170, typically about 140-160 ml/Kg/day.

The terms "increasing" or "enhancing" (e.g. body weight) refers to at least 0.05%, 0.1%, 0.5%, 1%, 2%, 5%, 10%, 15%, or 20% increase in an examined measure of the present invention including body weight, height, head circumference and gastrointestinal maturation of an infant compared to its expected value.

There are many different infant nutritional formulas that are commercially available or otherwise known in the infant formula art. These infant formulae comprise a range of nutrients to meet the nutritional needs of the growing infant, and typically include lipids, carbohydrates, protein, vitamins, minerals, and other nutrients helpful for optimal infant growth and development. While an effort is made to make the commercial infant formulae similar in composition to mature human milk, they are not identical, typically due to the formula processing conditions. Infant formulas may be produced as a powder that is reinstated into water, a concentrated solution that is diluted prior to use, or as a "ready-to-feed" solution.

The honey supplement of the invention may be orally administered alone, or in combination with breast milk or infant milk formula. In some embodiments, at least about 2 grams, at least about 5 grams, at least about 10 grams, or at least about 15 grams of honey is administered per day. In some embodiments, honey is mixed with infant formula or breast milk at a concentration of about 5 mg/ml to about 30 mg/ml, or about 10 mg/ml to about 25 mg/ml, or about 15 mg/ml to about 20 mg/ml.

In some embodiments, the infant is simultaneously or sequentially administered parenteral nutrition which includes intravenous administration of a liquid food mixture.

The term "medical-grade honey" refers to honey produced by bees that has been sterilized or purified. Sterilization or purification may be effected by filtration, e.g. through a 50 micron filter, and either pasteurization or gamma irradiation. The medical-grade honey is selected from a variety that includes, but is not limited to, Manuka, Pasture, Ling Kahami, Portobello, Greek Pine, Yorkshire, Chilean Ulmo, Chilean Rain Forrest, Australian *Eucalyptus*, Himalayan, Scottish Heather, Scottish Wild Flower, English Heather, English Wildflower, New Zealand Clover, Australian Clover, Cuban Comparitan, *Acacia*, Spanish Blossom, Tasmanian Leatherwood, Organic Honey All, New Zealand Beach, Kanuka, New Zealand Bush, New Zealand Honey Dew, Jarrah, Thyme, Kamahi and *Leptospermum* honeys of all varieties.

Prebiotics are non-digestible food ingredients that can selectively stimulate the growth of a number of beneficial bacteria in the intestine of the host.

In some embodiments, the composition of the invention comprises medical-grade honey as the prebiotic component and a probiotic component comprising beneficial microorganisms. Such compositions may be termed synbiotics.

Other prebiotic compounds may also be administered with the prebiotic honey formulation of the invention. Exemplary prebiotic compounds include, but are not limited to, oligosaccharides, such as fructooligosaccharides (FOS) and inulin.

Intestinal microbiota or "gut flora" refers to microorganisms that live in the digestive tracts of animals, and constitutes the largest reservoir of human flora. The symbiosis between the gastrointestinal tract and the large number of bacteria contributes substantially to normal digestive function. Thus, the gut flora serves as an effective barrier against opportunistic and pathogenic micro-organisms, and this 'colonization resistance' is one of their most important functions.

The normal flora presents an exceedingly complex equilibrium between the microorganisms that normally reside in the gastrointestinal tract, playing an important role in nutrition, physiology, and the regulation of the host's immune system. The bacteria are key components in promoting the early development of the gut's mucosal immune system in terms of both its physical components and function and continue to play a role in its operation, later in life. The bacteria stimulate the lymphoid tissue associated with the gut mucosa to produce antibodies to pathogens. The immune system recognizes and fights harmful bacteria, but does not act against the helpful/beneficiary species alone, a tolerance developed in infancy.

The term "promoting growth of non-pathogenic intestinal microbiota" is used to denote any one of enhancing, inducing, stimulating and similar effects on the construction and or generation of gut (intestine) flora in a subject. The gut flora in the context of the invention refers to bacterial gut population within at least a portion of the intestinal tract. In some embodiments, the abundance of Bifidobacteria and/or Lactobacilli in the gut flora is increased. In some further embodiments, the bacterial gut population is predominantly enriched with Bifidobacteria and/or Lactobacilli, meaning that Bifidobacteria and/or Lactobacilli are more abundant. Thus, in some embodiments the honey formulation in accordance with the invention increases the abundance of Bifidobacteria and/or Lactobacilli in the gut flora of the treated subject. The term "promoting growth of non-pathogenic intestinal microbiota" is also referred to herein as "promoting growth of beneficial intestinal microbiota". In some embodiments and aspects of the invention the beneficial gut flora may be essentially equivalent and/or comparable to gut flora of a breastfed subject.

In some embodiments, the honey formulation is effective to promote development of gut flora comprising predominantly Bifidobacteria and Lactobacilli. Other beneficial intestinal microbiota include, but are not limited to *Saccharomyces, Enterococcus, Streptococcus, Pediococcus, Leuconostoc, Bacillus*, and *Escherichia*.

By promoting the development of beneficial gut flora, a favorable effect also may take place against colonization of pathogenic bacteria. Thus, the honey formulation of the invention is also useful for reducing, inhibiting and/or eliminating the colonization of pathogenic bacteria in the gut. Such pathogenic bacteria that may be affected by the presence of favorable gut flora include, but are not limited to, coliform organisms, *Enterobacteria, Clostridia, Staphylococcus, Streptococci, Veillonella, Proteus, Pseudomonas, Shigella, Salmonella*, viruses, fungi, and parasites.

Further, the term "promoting growth of non-pathogenic intestinal microbiota" is to be understood as encompassing an effect on the gut pH level, e.g. a reduction of pH level in the gut. It is appreciated that in healthy breastfed infants the pH in the gut is typically between about 5.5 and 6.5. The pH of the gut may be determined based on stool samples obtained from the treated subject.

Yet further, the term "promoting growth of non-pathogenic intestinal microbiota" is to be understood as encompassing a beneficial effect on the immune system of subject, whereby at least one or more of the following is achieved: (i) treating at least one disorder of the immune system of the subject, the at least one disorder of the immune system being as a result of gut flora imbalance in the subject; (ii) strengthening the immune system of the subject. Gut flora imbalance may be exhibited by low level of flora as well as by an imbalance in the flora population etc. as compared to the flora of a healthy breastfed or full-term infant. The disorder may be a chronic or acute disorder, and it may be a disorder involved with a reduced or weakened (immune deficiency) or, on the other hand, elevated function of the immune system (hyper-immune system). Such disorder may be selected from the group consisting of inflammation, atopy (e.g. allergy, asthma, eczema, rhinitis and atopic dermatitis), feeding intolerance and infection without being limited thereto. When referring to strengthening of the immune system it is to be understood as including induction, stimulation, enhancement and the like of a weakened immune system as well as of a healthy immune system.

In the context of the present invention the term "treatment" or "treating" and the like are used herein to refer to obtaining a desired pharmacological and physiological effect on the subject, including prophylactic in terms of "preventing" or partially preventing an undesired condition or symptoms from developing and/or therapeutic in terms of "curing" partial or complete curing of an already existing undesired condition. The term "treating" is used within the context of this application as treatment of subjects who are healthy and/or suffer from a disorder, disease, or impaired physiological/medical condition.

By an "effective amount" or "therapeutically effective amount" of the honey prebiotic composition of the invention is meant a sufficient amount of the medical-grade honey to enhance growth of an infant and/or promote growth of non-pathogenic intestinal microbiota in an infant at a reasonable benefit/risk ratio applicable to any medical treatment. It will be understood, however, that the total daily usage of the compositions of the invention will be decided by the attending physician within the scope of sound medical judgment. The specific therapeutically effective dose level for any particular subject will depend upon a variety of factors including the disorder being treated and the severity of the disorder; activity of the specific composition employed; the specific composition employed, the age, body weight, general health, sex and diet of the subject; the time of administration and route of administration; the duration of the treatment; drugs used in combination or coincidental with the specific composition employed; and like factors well known in the medical arts. For example, it is well within the skill of the art to start doses of the compound at levels lower than those required to achieve the desired therapeutic effect and to gradually increase the dosage until the desired effect is achieved.

In some embodiments, the prebiotic composition is effective to promote beneficial gut flora development to obtain a gut flora profile that is essentially equivalent and/or comparable to pre-determined or known normal gut flora profile in a healthy infant having a normal birth weight. The normal gut flora profile is determined based on a pre-determined level from a group of healthy infants. A level that is essentially equivalent/comparable to that of a pre-determined normal profile includes deviations from the normal level of about 5%, at times, about 10% and even up to about 15% from the predetermined level. In some embodiments the method according to the invention is utilized for developing a gut flora profile that is essentially equivalent/comparable to that of a full-term infant and/or a breastfed infant.

In some embodiments, the method of the invention comprises providing the honey formulation to the infant for a period of time, e.g. for 2-3 weeks or longer, from day one to weeks or months following birth.

Exemplary uses of the honey formulation of the invention include, but are not limited to:
increasing brain growth and neurodevelopment of infants
decreasing viral-associated pulmonary damage
preventing and reducing the severity of atopic dermatitis in infants
reducing the risk for developing allergic disease
anti-diabetic therapy
preventing necrotizing enterocolitis in newborns
preventing and treating bacterial vaginosis
treating acute gastroenteritis in infants
reducing the risk for rhinovirus infections in preterm infants
protecting human colonic muscle from lipopolysaccharide-induced damage
protecting against and treating travelers' diarrhea
reducing the hospital stay of children with acute diarrhea
treating *C. difficile*-associated diarrhea
reducing the incidence of urinary tract infections in infants
reducing the incidence of infantile colic
preventing the development of irritable bowel syndrome symptoms
preventing endotoxin production and providing antifungal activity reducing the incidence of irritable bowel syndrome symptoms reducing the incidence of functional constipation reducing the duration of diarrhea associated with the use of antibiotics reducing the incidence of liver diseases associated with parenteral nutrition reducing the incidence of gastritis reducing the incidence of insulin resistance and hypercholesterolemia reducing the incidence of and treating acute gastroenteritis in infants reducing the frequency of proven sepsis, feeding intolerance and duration of hospital stay in preterm and term infants reducing the risk of upper respiratory illness and ear infections treating and reducing the incidence of recurrent pseudomembrane colitis infection caused by *C. difficile*

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLES

Example 1

Medically-graded honey supplementation formula to preterm infants as a prebiotic: A randomized controlled trial Introduction In this study, it was hypothesized that the introduction of medical-grade, spore-free honey to infants' milk formula would produce a bifidogenic effect and stimulate the immune response of premature infants. This prospective double-masked randomized trial aimed to: a) assess the effect of enteral honey on the intestinal microbiota and somatic growth of preterm infants, b) determine its impact on the immune system of preterm infants, and c) determine the optimal dose to achieve these effects.

Patients and Methods

Patients:

This pilot prospective randomized trial was approved by the Institutional Review Board at Cairo University Children's Hospital. Parental consent was obtained before enrollment of subjects. Subjects included in this trial fulfilled the following inclusion criteria: a) born prematurely with gestational age ≤34 weeks, b) their postnatal age was >3 days, c) parental wish to use milk formula with no intention to use maternal breast milk or to breast feed d) enteral feeds were started and well-tolerated but the feeding volume did not reach half of the goal feed. It is important to note that donor's breast milk banks are not available in the country of Egypt. Thus, the only feeding option for non-lactating mothers is the use of milk formula. Infants were excluded from the study if they had: a) maternal conditions suggestive of chorioamnionitis or peripartum infections, b) major chromosomal abnormalities or major congenital anomalies of the cardiovascular, pulmonary or central nervous system; including neuromuscular disorders and neural tube defects, b) intestinal atresia, tracheoesophageal fistulas, omphalocele, gastroschisis, and other major congenital GI anomalies, and c) sepsis, either before or during enrollment. None of the recruited subjects should receive antimicrobials at the time of enrollment.

Maternal and perinatal history was collected for each infant. Gestational age was estimated using the last menstrual date, ultrasonography and the Ballard scoring system performed in the first day of life. Anthropometric measurements were recorded for all subjects at recruitment and weekly throughout the study. Birth weight was measured just after delivery on a calibrated scale after daily zero adjustment. The length of the newborn was measured with the subject in the supine position and the head in contact with a fixed board while the angles were gently held to extend the legs. Head circumference was determined by applying a measurement tape around the head over the glabella and supraorbital ridges anteriorly and the occiput so that the maximal circumference can be recorded.

Randomization:

Using opaque sealed envelopes, subjects were randomized into four intervention groups: Group A received 5 grams of bee honey suspension daily for two weeks, Group B received 10 grams of bee honey suspension daily for two weeks, Group C received 15 grams of bee honey suspension daily for two weeks, and Group D included control subjects who received regular feeding without any modifications. Honey was added to a bottle of milk formula by one of the investigators. None of the managing team was aware of the group assignment of the infant. Pathology and microbiology personnel were not aware of the group assignment at the time of assays.

Feeding:

Infants were fed cow's protein-based premature formula (80 cal/100 ml) as requested by parents. Feeds were started according to unit protocol) every 2 hours and advanced until full feed goal calories of 120 cal/kg reached around 2-3 weeks of life. While advancing on enteral feeds, infants received parenteral nutrition.

Honey was added to milk formula according to the randomization arm the infant belonged to. Honey was added only when infants' enteral feeding was advanced to half of the full feeding goal.

Methods

Honey:

Unprocessed clover honey was used after being sterilized by the Egyptian Atomic Energy Authority via 25 kGy Cobalt-60 gamma radiation. This dose should not change the physical, chemical or mineral contents of the honey. However, it may alter moisture content, vitamins C and E, and hydroxymethylfurfural (HMF) compositions. After sterilization, the honey was further examined by the Egyptian Ministry of Health to confirm absence of *Clostridium botulinum* spores.

Blood Testing:

Complete blood count (CBC) was obtained for each subject at the day of enrollment and weekly for two weeks, resulting in three samples per subject. CBC was assayed using Sysmex KX-21N cell counter and its reagents (Kobe, Japan).

CD4 and CD8 cytokines in serum were measured at day of enrollment and weekly for two weeks. Two mls of blood were collected and allowed to clot at room temperature for 10-20 minutes and then centrifuged for 20 minutes at 2000-3000 RPM to collect serum. Sera were stored at $-20°$ C. until processing. ELISA was used to assess the concentrations of CD4 and CD8 in samples (Human cluster of differentiation (CD4 and CD8) ELISA Kits, San Diego, Calif., USA). Samples with unknown amounts of CD4 or CD8 were added to monoclonal antibody enzyme wells, which were pre-coated with a CD4 or CD8 monoclonal antibody and incubated. Then CD4 and CD8 antibodies with biotin were added and combined with Strepavidin-HRP to form immune complexes. The samples were washed to remove uncombined enzymes. Chromogen solutions A and B were added. The resulting chroma or color intensity positively correlated to the concentration of CD4 and CD8. Using the concentration of the standard solution and corresponding optical density (OD) values, a standard curve linear regression equation was calculated. Then, the regression equation was used with the OD values of samples to calculate the corresponding sample's concentration.

Stool Samples:

Stool samples were collected at the day of enrollment and weekly for two weeks to isolate and identify bacteria. There were 3 samples collected per subject. Fresh fecal samples were collected directly from the subject's diaper in two sterile containers. One container was sent to microbiology lab for cultures. The second container was frozen at $-80°$ C. to be used for the molecular detection of *Bifidobacterium bifidum* and *Lactobacilus* spp.

Isolation and Identification of Bacteria:

Pour plate technique was used to isolate the organisms. One gram of the feces was inoculated into 9 ml of thioglycolate (Oxoid, United Kingdom) broth, shaken and homogenized. Then, samples were serially diluted ten folds. One ml aliquot of each sample and its dilutions were plated into Man Rogosa Sharpe (MRS) agar (MRS; Oxoid, UK) for isolation of Lactobacilli. The MRS-Cys agar plates were supplemented with 0.05% L-cysteine hydrochloride and 50 μg mupirocin (Delchimica, Italy) per liter of MRS for isolation of Bifidobacteria. Mannitol salt agar (Oxoid, UK) was used for isolation of staphylococci and MacConkey agar (Oxoid, UK) was used for isolation of *Enterobacteriaceae*.

Inoculated MRS and MRS-Cys plates were incubated anaerobically (85% nitrogen, 10% hydrogen, 5% carbon dioxide) at 37° C. for 48-72 h in an anaerobic jar using Oxoid anaerogen compact gas packs (Oxoid, UK). Inoculated mannitol and MacConkey agar plates were incubated aerobically at 37° C. for 24 h. The approximate number of colonies of the different genera was counted and the bacterial burden was expressed as colony forming unit CFU/gm stool.

Colonies of different morphologies and sizes growing on MRS and MRS-Cys agar were chosen and transferred to MRS and MRS-Cys broth for incubation for 24 to 48 h anaerobically. Bacterial isolates were characterized on the basis of their morphology, microscopic appearance after gram staining and catalase reaction.

Gram Staining:

Fresh cultures were transferred aseptically into 1.5 ml Eppendorf tubes and centrifuged for 5 min at 6000 rpm. The supernatant was then removed and cells were re-suspended in sterile distilled water that was followed by application of the Gram staining procedure.

Slide Catalase Test:

This test was performed to confirm that lactic acid producing bacteria was catalase negative. Isolates growing on either mannitol salt agar or MacConkey agar were identified as members of the genus *Staphylococcus* or *Enterobacteriaceae* respectively by conventional methods.

Molecular Detection of *Bifidobacterium bifidum* and *Lactobacillus* spp:

Quantitative real-time PCR for *Bifidobacterium bifidum* and *Lactobacillus* spp DNA was performed at the National Research Center as follows:

DNA Extraction:

QIAamp® DNA Stool Mini Kit for DNA purification from stool samples (QIAGEN Group, Germany) was used for DNA extraction from the stool samples. Stool samples were lysed in buffer ASL. Then, DNA-damaging substances and PCR inhibitors in the stool sample were adsorbed to InhibitEX matrix. After inhibitors and DNA-degrading substances had been adsorbed to InhibitEX matrix, it was pelleted by centrifugation and the DNA in the supernatant was purified on QIAamp® mini spin columns. Proteins were digested and degraded during 70° C. incubation with proteinase K. Buffering conditions were then adjusted to allow optimal binding of DNA to the QIAamp® membrane, and the samples were loaded onto the QIAamp® spin column. DNA was adsorbed onto the QIAamp® silica membrane during a brief centrifugation step. DNA bound to the QIAamp® membrane was washed in two centrifugation steps to remove any residual impurities without affecting DNA binding. Then, purified DNA was kept at −20° C. for further testing.

On the day of the test, specimens were allowed to thaw at room temperature. Stool samples (200 mg each) were placed in a micro-centrifuge tube and 2 ml Buffer ASL was added to each tube. This was vortexed continuously until the stool sample was thoroughly homogenized. Then, 1.6 ml of the stool lysate was pipetted into a 2 ml micro-centrifuge tube. The suspension was heated for 5 min at 95° C., then vortexed for 15 s. The sample was centrifuged at full speed for 1 min to pellet stool particles. The lysis temperature was increased to 95° C. for cells that were difficult to lyse such as Gram-positive bacteria. Then, 1.2 ml of the supernatant were pipetted into a new 2 ml micro-centrifuge tube. One InhibitEX tablet was added to each sample and vortexed immediately and continuously until the tablet was completely suspended. The suspension was incubated for a minute at room temperature to allow inhibitors to adsorb to the InhibitEX matrix. Samples were centrifuged at full speed for 3 min to pellet stool particles and inhibitors bound to InhibitEX matrix. All of the supernatant was pipetted into a new 1.5 ml micro-centrifuge tube and the pellet was discarded. Samples were then centrifuged at full speed for 3 min; 15 μl proteinase K was pipetted into a new 1.5 ml micro-centrifuge tube and 200 μl of the supernatant was added into the 1.5 ml micro-centrifuge tube containing proteinase K. 200 μl buffer AL were added and vortexed for 15 seconds. Then it was incubated at 70° C. for 10 min. 200 μl of ethanol (96-100%) was added to the lysate, and mixed by vortexing. The complete lysate was applied to the QIAamp® spin column and centrifuged at full speed for 1 min. The QIAamp® spin column was carefully opened and 500 μl buffer AW1 was added without wetting the rim. The cap was closed and the tube containing the spin column was centrifuged at full speed for 1 minute. The QIAamp® spin column was placed in a new 2 ml collection tube and the collection tube with filtrate was discarded. The QIAamp® spin column was carefully opened again and 500 μl buffer AW2 was added. The tube containing the spin column was centrifuged at full speed for 3 minutes. This step was performed to eliminate any chance of possible buffer AW2 carryover, as residual buffer AW2 in the eluate may cause problems in downstream applications. The QIAamp® spin column was placed in a clean 1.5 ml micro-centrifuge tube, and the collection tube containing the filtrate was discarded. The QIAamp® spin column was opened carefully and 200 μl buffer AE was added directly onto the QIAamp® membrane and incubated at room temperature for 1 minute. The micro-centrifuge tube containing the QIAamp® spin column was then centrifuged at 8000 rpm for 1 minute. DNA concentration was measured in each DNA elute tube using a spectrophotometer. The eluted DNA was placed at −20° C. until PCR testing was performed.

Quantitative Real Time PCR:

PCR was done via the Applied Biosystem StepOne instrument (Applied Biosystems, Foster City, Calif., USA). First, the PrimerDesign™ (Genesig, Chandler's Ford, UK) kit for *Bifidobacterium* was used. The kit protocol was followed and detected *B. bifidum* via the FAM channel. A positive control template was used to generate a standard curve of *B. bifidum* copy number and CT value. If a negative result was obtained, the test results were deemed invalid and the rest was repeated. To confirm the absence of contamination, a negative control reaction was used with each kit. The same protocol was repeated for *Lactobacillus* spp. using the PrimerDesign™ (Genesig, Chandler's Ford, UK) kit.

Statistical Analysis: Comparison of numerical variables between the study groups was done using Student t test for independent samples. Paired t-test was used to compare repeated measures within the same group. ANOVA test was used for multiple comparisons. For comparing categorical data, Chi square ($\chi^2$) test was performed. Exact test was used instead when the expected frequency is less than 5. P values <0.05 were considered statistically significant.

Results

Forty preterm newborns were enrolled in the study with the intervention started during the $2^{nd}$ week of life in 22 infants and during the $3^{rd}$ week of life in 18 infants. The characteristics of the study population are presented in Table 1.

TABLE 1

Characteristics of the study population

| | Group A (n = 10) | Group B (n = 10) | Group C (n = 10) | Group D (n = 10) |
| --- | --- | --- | --- | --- |
| Gestational age (wk) [a] | 31.6 ± 1.1 | 29.7 ± 0.48 | 31.6 ± 1.1 | 29.9 ± 0.5 |
| Birth weight (kg) [a] | 1.49 ± 0.25 | 1.31 ± 0.06 | 1.53 ± 0.26 | 1.34 ± 0.06 |
| Length (cm) [a] | 40.3 ± 1.4 | 36.7 ± 1.2 | 39.3 ± 1.2 | 37.5 ± 0.4 |
| Head Circumference (cm) [a] | 28.4 ± 1 | 26.8 ± 1.3 | 28.7 ± 0.9 | 27.1 ± 0.5 |
| Sex (male) | 6 | 6 | 6 | 6 |
| Vaginal delivery | 6 | 5 | 6 | 7 |
| PPROM | 0 | 4 | 1 | 1 |
| Apgar at 1 min [b] | 6 (5-7) | 6 (5-6) | 7 (6-7) | 7 (7-8) |
| Apgar at 5 min [b] | 8 (7-8) | 9 (8-9) | 9 (9-9) | 9 (9-9) |
| Hemoglobin (g/dl) [a] | 13.31 ± 2.98 | 13.43 ± 0.57 | 17.33 ± 2.59 | 15.2 ± 1.41 |

PPROM = preterm premature rupture of membranes; data are expressed in numbers except with
[a] data are presented in mean ± SD and with
[b] data are presented in median (interquartile range).

At enrollment, the four groups did not differ in weight and the administration of honey was associated with significant weight increase. Compared to control group, groups B and C had significant increase in weight after one week (p<0.0001), and groups A, B and C had significant weight increase by two weeks (p<0.0001). No significant changes in length during the study except for group A at two weeks had greater increase compared to controls (p=0.009). Head circumference increased significantly in groups B and C when compared to group D after two weeks (p=0.0056) (FIG. 1).

CD4 and CD8 concentrations (ng/dl) did not differ among groups at enrollment or after two weeks of randomization (Table 2).

TABLE 2

CD4 count at days 0, 7 and 14 in the four studied groups

| Study day | Count | Group A | Group B | Group C | Group D |
|---|---|---|---|---|---|
| Day 0 | CD4 | 33.8 ± 93.6 | 1.17 ± 0.1 | 3.53 ± 1.6 | 2.7 ± 0.56 |
|  | CD8 | 13.44 ± 10.3 | 22.68 ± 16.9 | 11.98 ± 2.4 | 19.43 ± 10.5 |
| Day 7 | CD4 | 16.94 ± 36.5 | 2.49 ± 0.5 | 2.6 ± 2.4 | 2.55 ± 0.7 |
|  | CD8 | 16.53 ± 11.1 | 24.96 ± 12.9 | 13.98 ± 8.2 | 14.6 ± 7.1 |
| Day 14 | CD4 | 17.82 ± 31.1 | 2.95 ± 0.4 | 2.46 ± 0.7 | 2.61 ± 0.5 |
|  | CD8 | 14.55 ± 11.3 | 20.53 ± 13.6 | 14.91 ± 10.8 | 12.08 ± 2.1 |

Data are expressed in mean ± SD. No significant difference between groups for both of CD4 and CD8. Multivariate analyses were used.
CD4 = cluster of differentiation 4.
CD8 = cluster of differentiation 8.

Figure 2:
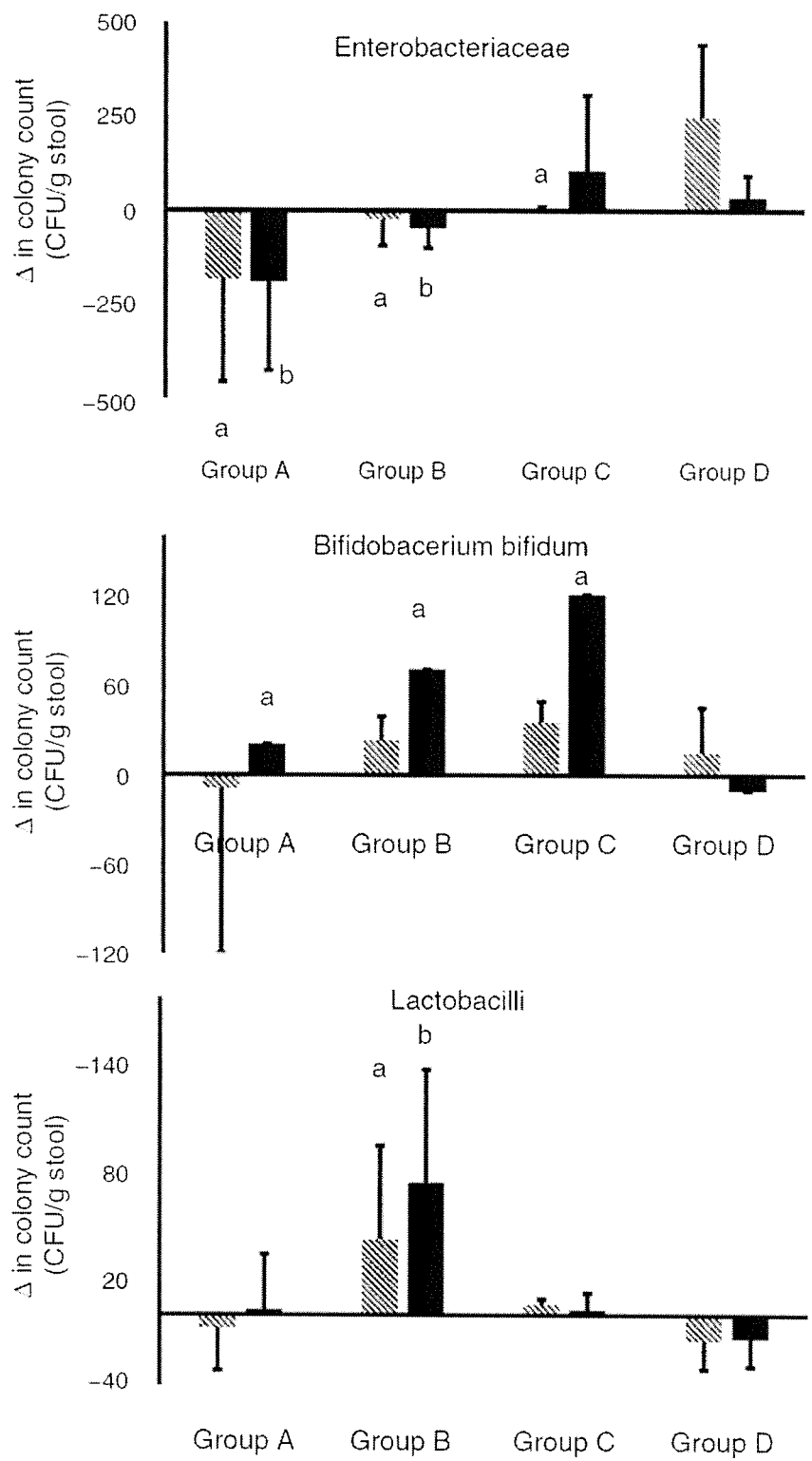
FIG. 2. Changes in bacterial colony count by culture in the 4 study groups after one and two weeks of enrollment. Dashed bars represent changes between baseline and one week. Solid bars represent changes between baseline and two weeks. Upper panel represents changes in *Enterobacteriaceae* (a): after one week of intervention, a significant decrease in colony count was recognized in the three intervention groups A, B and C ($p<0.0001$), and (b): after two weeks, only groups A and B continued to have less growth in colonies compared to group D ($p=0.002$). Middle panel represents changes in *Bifidobacterium bifidum*, (a): after two weeks, all three groups (A, B and C) had significantly greater colony growth compared to group D (p=0.002). Lower panel represents changes in Lactobacilli, (a): after one week, the number of colonies significantly increased in group B only (p=0.0007), and (b): after two weeks, the colony count increased in group B only (p<0.0001).

*Enterobacteriaceae* colony count by culture was significantly greater in group A before intervention. After one week of intervention, a significant decrease in colony count was recognized in the three intervention groups A, B and C ($p<0.0001$). After two weeks, only groups A and B continued to have less growth in colonies compared to group D ($p=0.002$)(FIG. 2).

*Bifidobacterium bifidum* colony count by culture did not differ among the four groups at baseline. After one week, colony counts in groups A, B and C did not differ from group D. After two weeks, all three groups (A, B and C) had significantly greater colony growth compared to group D ($p=0.002$). Lactobacilli mean colony number by culture was less in groups B and C compared to groups A and D ($p=0.015$). After one week, the number of colonies significantly increased in group B only ($p=0.0007$). After two weeks, the colony count increased in group B only ($p<0.0001$) (FIG. 2).

Applying RT-PCR, for *Bifidobacterium bifidum*, the copy numbers were similar in the four groups (A, B, C &D) at enrollment (8.6±11.1 vs. 33.7±46.6 vs. 8.4±2.6 vs. 14±8.3, respectively; $p=0.08$). The increase in copy number was significant in groups B and C when compared to group D after one week (59.6±67.6 and 65.9±7.3 vs. 7.3±11.4, respectively; $p=0.0001$). After two weeks, the increase in copy number was significant only in group C when compared to group D (1359±983.8 vs. 0.8±2.9; $p<0.0001$). For Lactobacilli, there was no difference among groups at enrollment with increased growth in groups B and C when compared to group D (112.6±142.9 and 53.3±26.1 vs. −4.1±8.5, respectively; $p=0.013$) after one week and in group C compared to group D after two weeks (1718.4±1434 vs. −6.4±7.6, $p<0.0001$).

DISCUSSION

This study demonstrated the introduction of medically-graded honey to cow's milk formula was associated with changes in microbiota of stool in premature infants. Infants who received honey had decreased colonization with *Enterobacteriaceae* and increased colonization with *Bifidobacterium bifidum* and Lactobacilli. Consumption of honey was associated with enhanced growth evidenced in increased weight gain and head circumference. There was no difference in CD4 and CD8 counts between the intervention and control groups.

In the present study, there was increased weight gain in the groups of infants receiving honey. The weight gain could be explained by increased caloric consumption in the groups of infants receiving honey. Previous trials demonstrated increased weight gain in infants receiving prebiotics. Other studies did not show any benefit of adding prebiotic combinations of galactooligosaccharides and fructooligosaccharides (GOS/FOS) or FOS alone on weight gain.

The present study showed that supplementing preterm formula with honey had no significant effect of on the linear growth of infants. This finding was similar to a recent meta-analysis that showed no effect on the linear growth when GOS/FOS were added to preterm formula, however, an effect was present when FOS was used alone. This study also showed that the intervention groups had a greater increase in head circumference than the control group. However, previous studies did not show any effect of prebiotics on head growth. Without being bound by theory, it is speculated that, in addition to the prebiotic properties, honey contains multiple trace elements that could have nootropic, synaptic plasticity, and anti-oxidant effects and may impact brain growth.

*Bifidobacterium bifidum* and Lactobacilli colonies in the stool of premature infants, as detected by culture and quantitative PCR were significantly increased with honey supplementation. This effect was even more pronounced in the groups of infants who received 10 g/d and 15 g/d but was not significant in infants who received 5 g/d (group A). Thus, the increased dose of honey is more efficacious in establishing this prebiotic effect. These findings are comparable to previously on the use of a mixture of GOS/FOS that showed a dose-dependent prebiotic effect. The synergic effect of honey on bifidobacteria could be partially reproduced when using the carbohydrate components of honey. Therefore, the prebiotic properties of honey are not restricted to its saccharide components.

*Enterobacteriaceae* colony count decreased in all of the three groups of infants who received honey within one week. However, after two weeks, this favorable effect did not continue in infants who received 15 g/d. Therefore, it seems this favorable effect of honey to decrease *Enterobacter* was dose dependent and was best achieved with 5 g/d and 10 g/d of honey. In fact, the dose of 15 g/d increased the growth of *Enterobacter* significantly after two weeks. It seems that the dose of 10 g/d was the optimal dose in this study; it decreased the growth of *Enterobacter* and had a positive bifidogenic effect.

This study is the first to examine the role of honey on the colonization of gut flora in human neonates. The study demonstrated the feasibility of using medical-graded sterilized honey to neonates.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A method for promoting growth of non-pathogenic intestinal microbiota in an infant comprising
    measuring a level of non-pathogenic intestinal microbiota in a stool sample obtained from the infant; and
    when the level of non-pathogenic intestinal microbiota is lower than a reference value obtained from healthy controls, administering to said infant medical-grade honey in an amount sufficient to promote growth of non-pathogenic intestinal microbiota in said infant, wherein the medical-grade honey is free of *Clostridium botulinum* spores.

2. The method of claim 1, wherein said non-pathogenic intestinal microbiota includes at least one of *Bifidobacterium* and Lactobacilli.

3. The method of claim 1, wherein said amount is an amount sufficient to decrease the growth of intestinal Enterobacteriaceae and Staphylococci.

4. The method of claim 1, wherein said infant is a low birth weight infant.

5. The method of claim 1, wherein said infant was born prematurely.

6. The method of claim 1, wherein said medical-grade honey is administered with infant milk formula or breast milk.

7. The method of claim 1, wherein said amount is at least 5 grams of medical-grade honey per day.

8. The method of claim 1, further comprising the step of simultaneously or sequentially administering parenteral nutrition to said infant.

9. The method of claim 1, wherein said amount is 5-15 grams of medical-grade honey per day.

* * * * *